United States Patent [19]

Steffensmeier

[11] Patent Number: 4,960,111

[45] Date of Patent: Oct. 2, 1990

[54] CHIROPRACTIC TABLE

[76] Inventor: Lloyd A. Steffensmeier, 102-122 W. Main St., Lisbon, Iowa 52253

[21] Appl. No.: 228,986

[22] Filed: Aug. 5, 1988

[51] Int. Cl.[5] ........ A61F 5/00

[52] U.S. Cl. ........ 128/72; 128/70; 128/74

[58] Field of Search ........ 128/70-74, 128/781, 782, 779, 774

[56] References Cited

U.S. PATENT DOCUMENTS

| | | | |
|---|---|---|---|
| 2,622,950 | 12/1952 | Nimms | 128/73 |
| 3,113,770 | 12/1963 | Rutledge | 128/72 |
| 3,998,218 | 12/1976 | Lane et al. | 128/70 |
| 4,122,840 | 10/1978 | Tsuchiya | 128/779 |
| 4,136,682 | 1/1979 | Pedotti | 128/779 |
| 4,314,552 | 2/1982 | Moon | 128/70 |
| 4,445,504 | 5/1984 | Barge | 128/70 |
| 4,489,714 | 12/1984 | Barnes | 128/70 |
| 4,579,109 | 4/1986 | Lundblad | 128/71 X |
| 4,723,537 | 2/1988 | Parker, Jr. | 128/70 X |
| 4,834,072 | 5/1989 | Goodman | 128/70 X |

*Primary Examiner*—Richard J. Apley
*Assistant Examiner*—Joe H. Cheng
*Attorney, Agent, or Firm*—James C. Nemmers

[57] ABSTRACT

An apparatus for treatment of certain physical conditions by a chiropractor or other health professional in which a patient support, such as a table with separate sections is used to apply a controlled, abrupt force, either singly or in programmed repetition, to assist the health professional in conducting certain procedures on the patient. Force is applied to the patient manually by the health professional but also through the cushion on a separate section of the patient support by means of a double-acting force applying means, such as a hydraulic cylinder. Both the force generated by the apparatus and the total force applied to the patient is displayed so that the health professional can accurately control the procedure and achieve the desired result. The system can be programmed so as to apply a selected number of successive forces at a relatively high rate.

7 Claims, 2 Drawing Sheets

FIG. 1
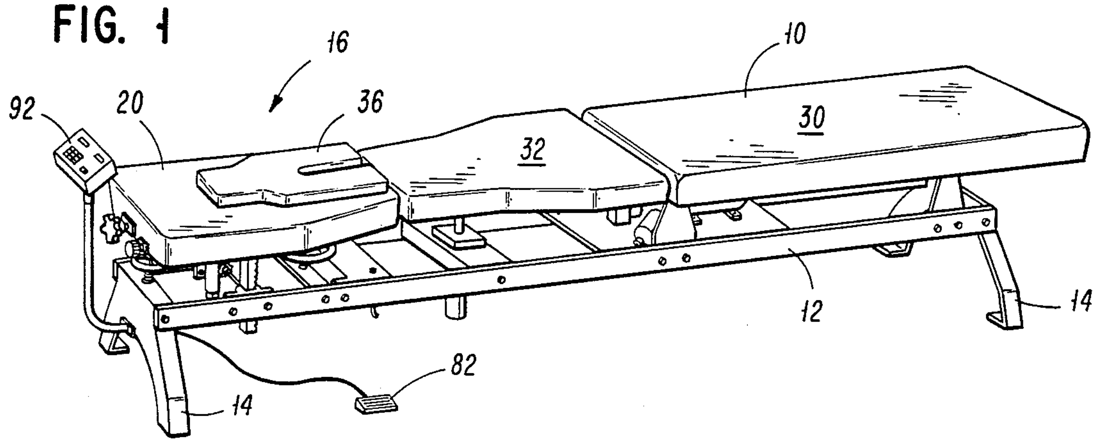
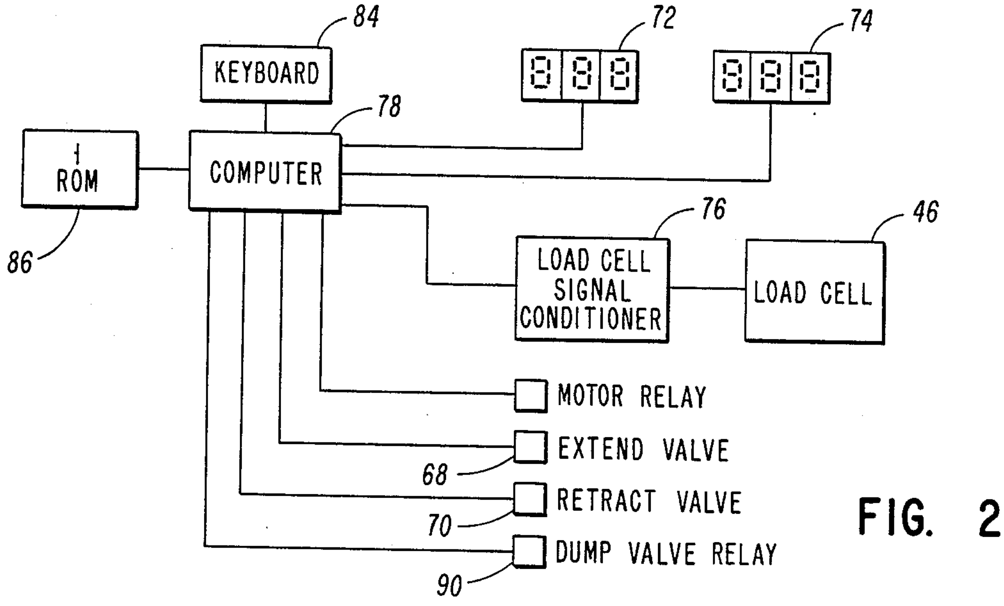
FIG. 2
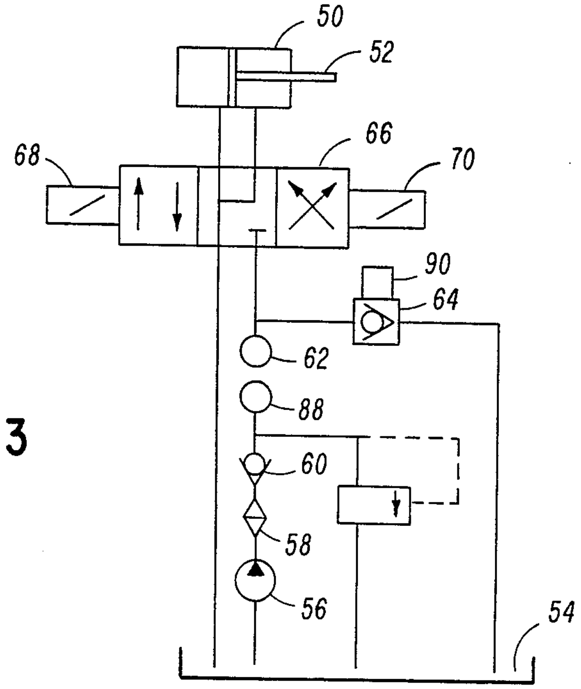
FIG. 3

CHIROPRACTIC TABLE

BACKGROUND OF THE INVENTION

Numerous types of patient supports, such as tables, are available to enable the practicing chiropractor or other health professional to conduct examinations, adjustments and treatments beneficial to the patient. Most patient supports or tables are designed so that a separate section, such as a headpiece or thoracic, lumbar, pelvic or other section, is movable so that the health professional can conduct the desired adjustment or treatment upon a given part of the patient's body. In tables designed for conducting certain prescribed adjustments and treatments, the separate section has a movable mechanism that allows that section to be displaced predetermined distance to facilitate the adjustment. Since the tables, including the separate headpiece or other section, are generally provided with cushions, the cushions tend to absorb some of the forces manually applied by the health professional. It is therefore difficult for the health professional to accurately control the amount of force applied.

Improvements have been made in chiropractic adjustment tables, such as the one disclosed in Barge U.S. Pat. No. 4,445,504. This patent discloses a table in which a separate section is provided with actuating means that will abruptly and rapidly move the cushion a controlled distance. This is accomplished by the use of a cylinder the operating rod of which is affixed to the base of the cushion. When the cylinder is actuated by the chiropractor through suitable actuating means, the cushion will be suddenly and rapidly moved within a predetermined distance. When this force is applied simultaneously with the health professional manually applying a resisting force at the appropriate place on the patient, the health professional is able to conduct the proper spinal or body adjustment, and consistently and uniformly apply the same adjustment to that patient in future treatments as well as to other patients needing similar treatment.

Although the Barge Table is a substantial advance over the then existing state-of-the-art, health professionals using the Barge Table cannot determine, except by experience and feel, the total amount of force being applied to the patient. Moreover, as research and knowledge in the various health fields progress, it is becoming apparent that there are procedures where forces applied in rapid succession have therapeutic benefit for the patient. In any event, it would be desirable for the health professional to be able to accurately determine and measure the total force being applied to the patient and also to program the number of repetitions and the rate of repetitions of the measured force in a particular procedure.

It is therefore a object of the invention to provide an improved patient examination and treatment table in which the health professional can determine accurately and consistently the amount of total force being applied to the patient during a given procedure.

It is a further object of the invention to provide an improved health examination and treatment table in which the health professional can apply successive and controlled thrusts in an extremely short period of time, while still controlling the force applied.

These and other objects and advantages of the invention will become readily apparent from the detailed description and operation of the invention set forth hereinafter.

SUMMARY OF THE INVENTION

The health care apparatus of the invention provides a system in which a double-acting hydraulic cylinder is operatively connected to a separate section of a patient treatment table. A load cell combined with a force applying device, such as a hydraulic cylinder, and the section of the table to which it is connected accurately measures the total force applied through the table section to the patient by the hydraulic cylinder and by the hands of the health professional. This total force is continuously displayed so that the health professional at all times will know the total amount of force being applied to the patient. The hydraulic system also includes a control system which can be programmed to actuate the force applying device a predetermined number of times at a predetermined rapid rate upon receipt of a single signal from the health professional. With the system of the invention, the health professional can program the treatment for the patient, which treatment can be consistently applied and accurately recorded on the patient's chart. This permits the health professional to accurately control the treatment depending upon the patient's condition and progress.

BRIEF DESCRIPTION OF THE DRAWINGS

FIG. 1 is a perspective view of a chiropractic table constructed according to the principles of the invention:

FIG. 2 is a schematic diagram of the control system used to carry out the principles of the invention;

FIG. 3 is a schematic diagram of the hydraulic system used in carrying out the principles of the invention.

DESCRIPTION OF THE PREFERRED EMBODIMENT OF THE INVENTION

Figure 4:
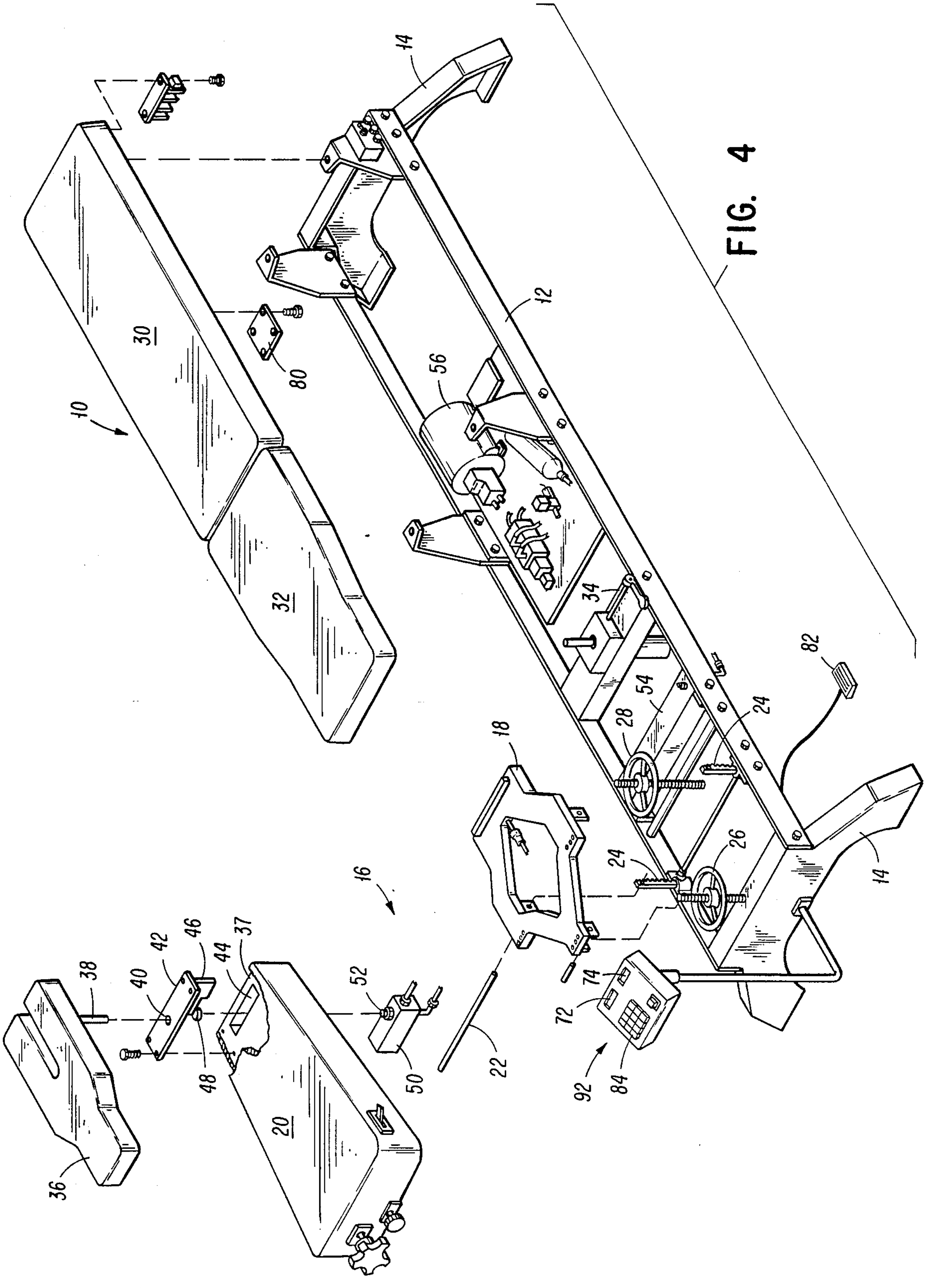
FIG. 4 is an exploded view of a chiropractic table constructed according to the principles of the invention and illustrating the various components used in the preferred embodiment of the invention.

The invention relates to and can be employed in connection with any patient support, such as a table or chair, that is used for the examination or treatment of the patient. The preferred embodiment of the invention is described herein in connection with a chiropractic table that has separate sections. Referring now to the drawings, and especially FIG. 1 and FIG. 4, there is illustrated a chiropractic table of the side-posture type which has a table bed 10 supported on a frame 12 that is in turn supported by legs 14. The table bed 10 is padded or otherwise cushioned for the comfort of the patient.

At the head end of the table is a separate headpiece indicated generally by the reference numeral 16. The headpiece 16 includes a rigid support base 18 to which is affixed a cushion 20. As best seen in FIG. 4, base 18 is pivotally mounted near its center on rod 22 which is supported at its outer ends by adjustable supports 24 that are in turn secured to the frame 12. The head end of the base 18 is also pivotally mounted on a manually adjustable support 26, and similarly, the end of base 18 opposite the head end is vertically adjustable by the manually adjustable support 28. Thus, with a patient placed on the table bed 10 in a side-posture position facing to the side, the patient's head will be supported by the headpiece 16 which can be adjusted both in height and tilt to the proper and desired position. If desired, the table bed 10 can be provided with two separate cushions 30 and 32, cushion 30 being adjustable in height using the adjusting mechanism indicated at 34. Use of the adjustment 34 sometimes eliminates the need for additional adjustments of headpiece 16. Cushion 30 is generally not adjustable in a table of this type.

The invention relates to the mechanism for applying a single force or repeated forces at a given rate to the head of the patient when the patient is properly positioned on the table. To accomplish this, the headpiece 16 is provided with an additional head cushion 36 positioned on top of cushion 20. As best seen in FIG. 4, the distal end of cushion 36 is provided with a support rod 38 extending downwardly through a guide opening 40 in load plate 42 which is affixed to the base 37 of cushion 36. The rod 38 permits the cushion to be rotated as desired for the comfort of the patient. The base 37 of cushion 36 has an opening 44 extending through it to receive a load cell 46 affixed beneath the load plate 42. Load cell 46 is a transducer of any known design that will convert force applied to it into an electrical signal proportional to the force. Preferably, load cell 46 is of the type that utilizes a strain gauge the electrical resistance of which changes in direct proportion to the bending force applied to it. The load cell 46 thus will measure the total force applied to the head cushion 36, including the weight of the patient's head and any force applied to the patient by the health professional. In use, the weight of the patient's head is isolated so that the apparatus can be calibrated to accurately measure the manual force applied to the patient's head by the health professional.

Mounted beneath the base 18 of the headpiece 16 is a force-applying device such as a double-acting hydraulic cylinder 50 which has a vertically extending operating rod 52. Operating rod 52 engages the operating arm 48 of load cell 46, and thus applies force to the operating arm 48 and to the load plate 42 which supports the head cushion 36. Thus, any force or thrust applied by hydraulic cylinder 50 will be applied directly to the distal end of the head cushion 36 while at the same time the applied force will be measured by the load cell 46.

Controlled force is applied through the hydraulic cylinder 50 to the head cushion 36 by means of a hydraulic system which is schematically shown in FIG. 3 of the drawings. A tank or reservoir 54 is mounted on the table frame 12 and provides a source of hydraulic fluid for the system. Hydraulic pump 56 pumps the hydraulic fluid from the reservoir 54 through the closed hydraulic system at a predetermined pressure. The amount of pressure in the system, and thus the amount of force applied by hydraulic cylinder 50 to the head cushion, is predetermined by the design of the hydraulic system. Hydraulic fluid is pumped by pump 56 from the reservoir 54 through a filter 58 and through a check valve 60 into an accumulator 62. A dump valve 64 returns fluid to the reservoir 54. The pressurized hydraulic fluid is passed through a four-way control valve 66 to the hydraulic cylinder 50. Valve 66 is actuated by solenoid 68 to extend the operating rod 52 or by solenoid valve 70 to retract the operating rod 52. Valves of this type are commercially available which are capable of stroking in 1/50th of a second. Thus, when solenoid valve 68 receives a signal and in turn causes the operating rod 52 to extend, a second signal can be received from the control circuitry to retract the operating rod 52 in 1/50th of a second. Also, the stroke of the cylinder 50 will depend upon the purpose for which the hydraulic cylinder 50 and four-way valve 66 are designed. For example, for the head cushion 36, the hydraulic cylinder 50 preferably has a stroke of approximately 3/16 of an inch, but this may be different for different sections of the table. This short stroke applied to a head cushion is sufficient to produce the desired effect for proper treatment of the patient.

Referring now to FIG. 2, the schematic of the control system is shown and operates as follows. As previously described, the load cell 46 continuously monitors the amount of force applied to the head of the patient resting on the head cushion 36. The force measured is the force applied manually by the health professional, which force is displayed on the digital display 72. This force can be calibrated, if desired, to eliminate the head weight of the patient. The load cell 46 will also measure the force applied to the head cushion 36 by the hydraulic cylinder 50. This force combined with the force manually applied by the health professional is displayed on display 74, which will then show the total maximum force applied to the patient. Obviously, the health professional can control this total force by the amount of manual force being applied, the force applied by the hydraulic cylinder being known. During the procedure, the health professional can either increase or decrease the manually applied force to the desired total force, this total force at all times being visible on the display.

The information from the load cell 46 is processed through a conditioner 76 into a central processing unit or computer 78. The specific design of the computer 78 does not form a part of the invention, and it is within the skill of persons in the art to design the circuitry to accomplish the desired purpose. Preferably, the circuit is predesigned on a circuit board 80 mounted on the table beneath the cushion 30. The computer 78 is designed so that it can be programmed to apply a single force each time the operating foot pedal 82 is actuated by the user, or by using keyboard 84 (or suitable dials), the computer can be programmed to produce the electrical signals to operate the four-way valve 66 so that the hydraulic cylinder 50 will apply successive forces of a predetermined number at a predetermined rate. For example, programming the computer 78 by using keyboard 84, the health professional may program four successive thrusts in a period of four seconds, one each second. So, by use of an appropriate ROM 86, the particular programming of the computer 78 can be changed.

Preferably, the hydraulic system (FIG. 3) is provided with a pressure switch 88 that will maintain a consistent pressure in the hydraulic system by providing a signal to the computer 78 to start and stop the motor for hydraulic pump 56 in order to maintain the pressure in the hydraulic system nearly constant. Constant pressure will also be controlled by computer 78 by actuation of the dump valve 64 through coil 90.

As a convenience, the displays 72 and 74 together with the keyboard 84 are preferably all mounted on a single operating panel 92, as shown in FIGS. 1 and 4.

Use of the system of the invention by a health professional to carry out the desired treatment by consistently and precisely controlling the application of force to the patient should be evident from the foregoing description. By being able to constantly monitor the amount of force that the health professional applies to the patient by using his hands, the health professional can determine and apply a proper course of treatment knowing at all times precisely what treatment has been made by recording the force displayed. By observing the results, the treatment can be continued or modified. Thus, with the system of the invention, the health professional has the capability of more precisely controlling the treatment and correlating the treatment according to the results produced. None of the prior art references show systems that allow the health professional to measure and record what was done during the course of any particular treatment. The use of the system of the invention thus minimizes the amount of professional judgment that must be exercised by the health professional and permits a more effective course of treatment to be utilized.

Having thus described the invention in connection with the preferred embodiment thereof, it will be evident to those skilled in the art that various revisions and modifications can be made to the preferred embodiment without departing from the spirit and scope of the invention. For example, the principles of the invention can be applied not only to the headpiece, but to any separate section of a health treatment table or chair. It is my intention however that all such revisions and modifications as well as uses for the invention will be included within the scope of the following claims.

What is claimed is as follows:

1. An apparatus for assisting a health professional in the treatment of a patient by applying force to a selected part of the patient's body, said apparatus comprising: patient support means to support the portion of the patient'body to be treated, force-applying means for exerting a controlled force on the patient by abruptly moving the patient support means a predetermined distance from an initial position and returning it to the initial position during a single cycle of the force-applying means, computer means having means for automatically repeating a cycle of the force-applying means, means operable by the health professional for selecting the amount of the force exerted by the force-applying means, means for controlling the number and rate of the cycles of the force-applying means and means for measuring and displaying the total force applied to the patient by the force-applying means during a cycle and the force manually applied to the patient by the health professional, and means operable by the health professional for controlling the rate of the application of the force applied to the patient.

2. The apparatus of claim 1 in which the means for measuring and displaying the total force applied to the patient includes a load cell that provides an output signal proportional to the applied force.

3. The apparatus of claim 2 in which the force-applying means includes a double-acting hydraulic cylinder having an operating rod operatively connected with the patient support means, the load cell being positioned to measure the force applied by the hydraulic cylinder as well as force applied to the patient support means by the weight of the patient and the force manually applied by the health professional to the patient.

4. The apparatus of claim 1 in which the patient support means is a table having a separately adjustable and moveable head piece.

5. The apparatus of claim 4 in which the means for controlling the force exerted by the force applying means is a keyboard operable by the health professional.

6. The apparatus of claim 1 in which the means for selecting the amount of force exerted by the force-applying means is a keyboard operable by the health professional.

7. The apparatus of claim 6 in which the means operable by the health professional for controlling the rate of the application of the force applied to the patient is a foot operated switch.

* * * * *